(12) United States Patent
Cai et al.

(10) Patent No.: US 10,156,538 B2
(45) Date of Patent: Dec. 18, 2018

(54) CONTROL METHOD AND SYSTEM FOR TEST STRIP ELECTRODES

(71) Applicant: SINOCARE INC., Changsha, Hunan (CN)

(72) Inventors: Xiaohua Cai, Hunan (CN); Hongli Che, Hunan (CN); Yongsheng Dai, Hunan (CN); Zecun Huang, Hunan (CN); Wei Zhang, Hunan (CN)

(73) Assignee: SINOCARE INC. (CN)

( * ) Notice: Subject to any disclaimer, the term of this patent is extended or adjusted under 35 U.S.C. 154(b) by 260 days.

(21) Appl. No.: 14/888,399

(22) PCT Filed: Apr. 21, 2015

(86) PCT No.: PCT/CN2015/077044
§ 371 (c)(1),
(2) Date: Oct. 30, 2015

(87) PCT Pub. No.: WO2016/082441
PCT Pub. Date: Jun. 2, 2016

(65) Prior Publication Data
US 2016/0334355 A1    Nov. 17, 2016

(30) Foreign Application Priority Data

Nov. 27, 2014  (CN) .......................... 2014 1 0697622

(51) Int. Cl.
*G01N 27/327*     (2006.01)
*G01N 27/30*      (2006.01)

(52) U.S. Cl.
CPC ....... *G01N 27/301* (2013.01); *G01N 27/3271* (2013.01); *G01N 27/3272* (2013.01); *G01N 27/3273* (2013.01); *G01N 27/3274* (2013.01)

(58) Field of Classification Search
CPC .................................. G01N 27/3327–27/3274
See application file for complete search history.

(56) References Cited

U.S. PATENT DOCUMENTS

2004/0232009 A1* 11/2004 Okuda ............... G01N 27/3274
                                                    205/789

FOREIGN PATENT DOCUMENTS

| CN | 1633596 A | 6/2005 |
|---|---|---|
| CN | 103487476 A | 1/2014 |
| CN | 203724101 U | 7/2014 |
| CN | 10440702028 A | 3/2015 |
| WO | WO2004093784 A2 | 4/2004 |

* cited by examiner

*Primary Examiner* — J. Christopher Ball

(57) ABSTRACT

The disclosure includes a control method for test strip electrodes. The method can include inserting a test strip into a glucose meter and applying a predetermined voltage to the working electrode W of the test strip. The Method can also include applying a sample to the test strip and acquiring real-time data of current generation at the electrodes R1 and R2 of the test strip. Some embodiments can also include determining whether the electrode R1 generates current earlier than the electrode R2 or not.

1 Claim, 7 Drawing Sheets

CONTROL METHOD AND SYSTEM FOR TEST STRIP ELECTRODES

BACKGROUND OF THE INVENTION

Technical Field

The present invention relates to the technical field of blood-glucose testing, and more particularly, to a control method and system for test strip electrodes.

Description of Related Art

Referring to FIG. 1, the blood-glucose test strip has three electrodes: a working electrode W, a background electrode B, and a reference electrode R, arranged into an inverted triangle. In an optimized arrangement, the background electrode B and the reference electrode R are placed at the base angles, respectively, of the inverted triangle while the working electrode W is placed at the vertex.

In testing the blood-glucose of blood samples in a blood glucose test strip with a glucose meter, the three electrodes have their own functions. The reference electrode can be grounded with the voltage of 0 V. The working electrode W and the background electrode B can be applied with different working voltages. A circuit can be formed between the reference electrode R and the working electrode W to generate testing current signals. A circuit can be formed between the background electrode B and the reference electrode R to generate correcting current signals, which are used for correcting the testing current signals. Corrected testing current signals can be subsequently used to obtain the content of the blood glucose in the blood samples.

However, the test strip has such an extra wide sampling opening that blood samples can enter the reaction chamber from any part of the front side of the test strip. As such, blood samples may contact the background electrode B first or may contact the reference electrode R first. Thus, testing current signals will be affected by the direction of sampling due to the randomness of sample application Specifically, referring to FIG. 2, if a blood sample contracts the background electrode B (e.g. the sample is introduced from the left), neither electrode generates current signals when the background electrode B is covered but the reference electrode R is not in contract with the blood sample. As well, when the reference electrode R contacts the blood sample, detection signals and correcting signals are generated at the same time, and the intensity of the two signals can depend on the extent to which the reference electrode R is covered by the blood sample, so the intensity of the two signals is well matched and testing results are accurate. If a blood sample contacts the reference electrode R first (e.g. the sample is introduced from the right), the two signals at the working electrode W and the background electrode B are generated at different time points. When the background electrode B makes contact with the blood sample, the reference electrode R has already been completely filled, and at this time, the signal on the reference electrode R has reached the highest intensity (i.e. detection signals have reached the highest intensity). Since the background electrode B is affected by the amount of the blood sample and the time of sample suction, its coverage extent cannot be controlled, causing mismatching of intensity between detection signals and correcting signals and affecting the accuracy of testing results, which can lead to inaccurate testing results of the content of the blood glucose and a waste of test strips.

BRIEF SUMMARY OF THE INVENTION

Given this, the objective of the present invention is to provide a control method and system for test strip electrodes so as to overcome the drawbacks of glucose meters in the prior art, i.e. low testing accuracy and a waste of test strips.

To solve the technical problems above, the present invention provides a control method for test strip electrodes. The disclosure can include a control method for test strip electrodes. In some embodiments, the method includes inserting a test strip into a glucose meter; applying a predetermined voltage to the working electrode W of the test strip; applying a sample to the test strip; acquiring real-time data of current generation on the electrodes R1 and R2 of the test strip; and determining whether the electrode R1 generates current earlier than the electrode R2. If electrode R1 generates current earlier than electrode R2, a first control command can be sent to set the electrode R1 as the background electrode B and the electrode R2 as the reference electrode R. If electrode R1 does not generates current earlier than electrode R2, a second control command can be sent to set the electrode R1 as the reference electrode R and the electrode R2 as the background electrode B.

In some embodiments, acquiring the real-time data of current generation on the electrodes R1 and R2 can further comprise setting the working electrode W to output a voltage of 300 mv continuously, and setting the electrode R1 and the electrode R2 to be alternately grounded every 10 ms. The ungrounded electrode of R1 and R2 can be suspended. Methods may also include setting the current detection of the grounded electrode of R1 and R2 in a real-time manner to acquire the real-time data of current generation of electrode R1 or R2 while the electrode R1 or electrode R2 is grounded.

Prior to determining whether the electrode R1 generates current earlier than the electrode R2, methods may include determining which of the R1 and R2 electrode generated current first, and under the pre-set conditions; monitoring the R1 and R2 electrode, which did not generate current; and conducting error message reporting if no current is detected for the electrode over the predetermined duration.

In some embodiments, the step that under the pre-set conditions, monitoring the R1 and R2 electrode, which did not generate current, and conducting error message reporting if no current is detected for the electrode over the predetermined duration. Methods may include once current is detected at R1 or R2, terminating application of the voltage to the working voltage W, keeping R1 and R2 grounded, and waiting for a 80 ms delay; after the delay, setting the working electrode W to output a pulse in the form of 300 mv-0 mv, setting R1 and R2 electrode, which generated current first as suspended and the other electrode as grounded; and acquiring the data on the current generation of the grounded electrode, and if no current is generated on the ground electrode over 1.5 s, conducting error message reporting.

After the first control command or the second control command is sent, methods can further include setting both the working electrode W and the background electrode B of the test strip to output a voltage of 0 mv for 200 ms.

The disclosure can also include a control system for test strip electrodes, comprising: an acquisition module for acquiring the real-time data on current generation of the R1 and R2 electrodes of the test strip after inserting a test strip into a glucose meter, applying a predetermined voltage to the working electrode W of the test strip, and applying a sample to the test strip; a determination module for determining whether the electrode R1 generates current earlier than the electrode R2 or not; a first control module for sending the first control command to set the electrode R1 as the background electrode B and the electrode R2 as the reference electrode R if electrode R1 generates current earlier than the electrode R2; and the second control module for sending the second control command to set the electrode R1 as the reference electrode R and the electrode R2 as the background electrode B if electrode R1 does not generate current earlier than electrode R2.

In some embodiments, the acquisition module further comprises a first control unit for setting the working electrode W to output a voltage of 300 mv continuously, and setting the electrode R1 and the electrode R2 to be grounded alternately every 10 ms, and setting the R1 and R2 electrode that is not grounded as suspended; and an acquisition unit for controlling the current detection of the grounded R1 and R2 electrode in a real-time manner to acquire the real-time data on current generation of the electrode R1 or R2 while the electrode R1 or electrode R2 is grounded.

Some embodiments can also include an error message reporting module for determining the electrode of R1 and R2 which generates current first, and under the pre-set conditions, monitoring the R1 and R2 electrode did not generate current, and conducting error message reporting if no current is detected for the electrode over a predetermined duration.

The error message reporting module can further comprise a delay-wait unit for stopping applying voltage to the working voltage W, keeping R1 and R2 grounded, and waiting for a 80 ms delay, once current is detected at R1 or R2; a second control unit for setting the working electrode W to output a pulse in the form of 300 mv-0 mv, setting the R1 and R2 electrode which generated current first as suspended and the other electrode as grounded after the delay; and the error message reporting unit for acquiring the data on current generation of the grounded electrode, and if no current is generated at the grounded electrode over 1.5 s, conducting error message reporting.

In some embodiments, the control system also includes a delay module for setting both the working electrode W and the background electrode B of the test strip to output a voltage of 0 mv for 200 ms.

DETAILED DESCRIPTION OF THE INVENTION

To help better understand the present invention, the preferred embodiments of the present invention will be detailed hereinafter with examples, but it should be understood that the description is for further describing the features and advantages of the present invention only, rather than limiting the claims of the present invention.

In the control method and system for test strip electrodes according to the present invention, the real-time information about current generation at the electrodes R1 and R2 of the test strip is acquired after inserting a test strip, applying a predetermined voltage to the working electrode W of the test strip and applying a sample to the test strip, and determination is made as to which electrode generates current first; if the electrode R1 generates current first, R1 is controlled as the background electrode and R2 is controlled as the reference electrode; otherwise, R1 is controlled as the reference electrode, and R2 is controlled as the background electrode. It can be seen that the present invention can realize reasonable control of the electrodes of a test strip based on the direction of sampling so as to control the electrode close to the direction of sampling (background electrode or reference electrode) as the background electrode, avoiding the problems where the detection signals and correcting signals are not generated at the same time and of mismatching of intensity between detection signals and correcting signals. Therefore, in application of the present invention, when samples are introduced into a test strip from various directions, it can be ensured that the testing result of the blood-glucose content has high accuracy.

Embodiment I

Figure 1:
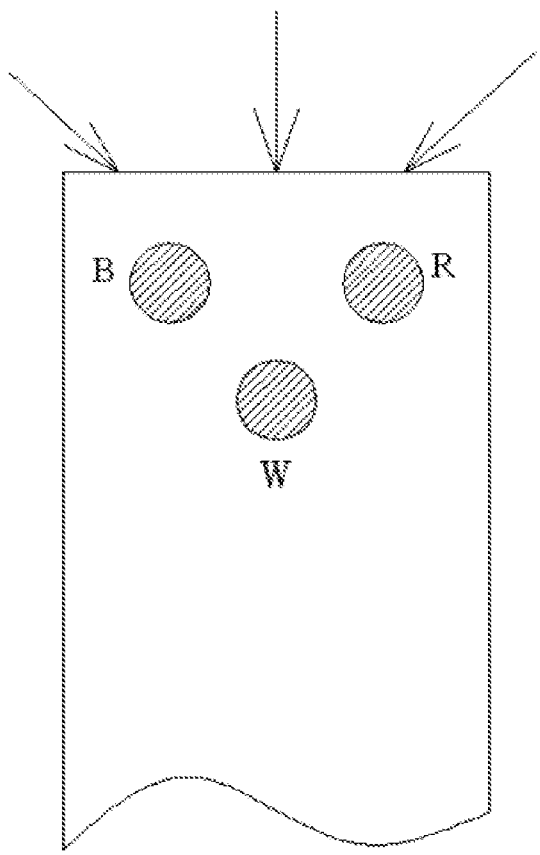
FIG. 1 is a schematic diagram of the electrodes in a blood-glucose test strip in the prior art.
Figure 2:
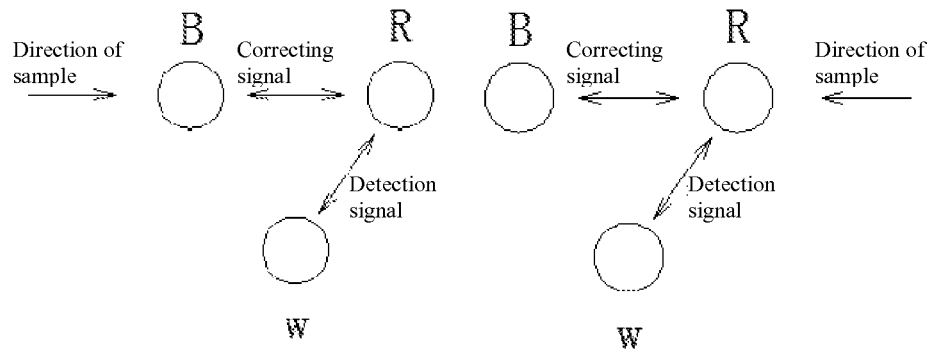
FIG. 2 illustrates introduction of a sample from different directions in testing blood glucose with a blood-glucose test strip in the prior art.
Figure 3:
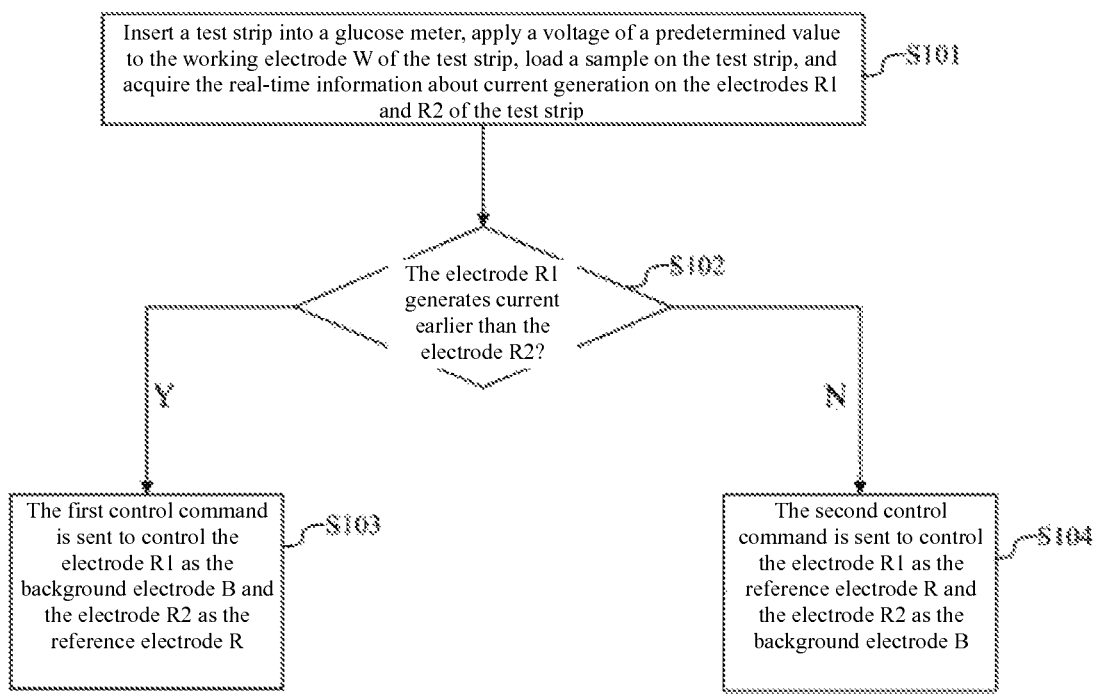
FIG. 3 is a flow diagram of a control method of test strip electrodes disclosed in Embodiment I of the present invention.

Embodiment I of the present invention discloses a control method for test strip electrodes. Referring to FIG. 3, the method includes: inserting a test strip into a glucose meter, apply a predetermined voltage to the working electrode W of the test strip, applying a sample to the test strip, and acquire the real-time information about current generation on the electrodes R1 and R2 of the test strip (at Step S101).

Figure 4:
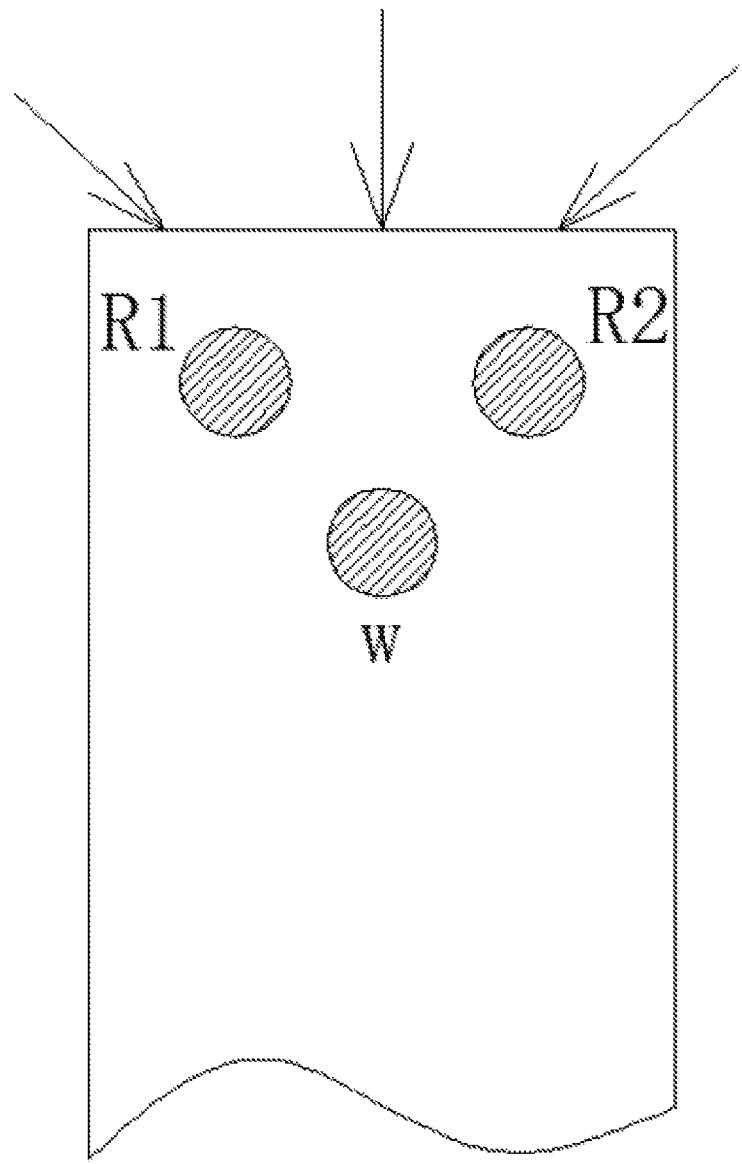
FIG. 4 is a schematic diagram of the electrodes of a blood-glucose test strip disclosed in Embodiment I of the present invention.

Specifically, an ABA-type test strip can be used in this embodiment to detail the method of the present invention. As shown in FIG. 4, the electrode R1 and the electrode R2 can be arranged on the left side and the right side of the strip respectively or vice versa, and the working electrode W is arranged in the middle of the strip.

After insertion of a blood-glucose test strip into a glucose meter, the working electrode W of the test strip can be continuously applied with a voltage of 300 mv. During application, a sample can be introduced into the test strip, which can be followed by a process of waiting for sample absorption. For example, R1 and R2 can be alternately grounded every 10 ms with the aim of removing interfering signals, and ungrounded electrode can be suspended.

At the same time, while R1 or R2 is grounded, the method can include carrying out current detection correspondingly for R1 or R2 to determine whether R1 or R2 generates current. After one electrode is determined to have generated current, the method can include keeping the electrode, which generates current grounded, and carrying out current detection at the electrode every 10 ms to perform confirmation twice (a duration of 20 ms) so as to make sure that the current signals detected are not interfering signals. Sampling can be deemed to be effective after current confirmation for twice.

Methods can also include determining whether the electrode R1 generates current earlier than the electrode R2 (at Step S102). The step can determine which electrode generates current first based on Step S101 of carrying out real-time current detection for the electrode R1 and R2.

If the determination result is yes, the first control command can be sent to control the electrode R1 as the background electrode B and the electrode R2 as the reference electrode R (at Step S103). If the determination result is no, the second control command can be sent to control the electrode R1 as the reference electrode R and the electrode R2 as the background electrode B (at Step S104).

If the electrode R1 is detected to generate current first, then it demonstrates that the user introduces the sample into the test strip from the left, the electrode R1 can be covered by the blood sample earlier than R2, and the electrode R1 can be well covered by the blood sample. In order to ensure that the electrodes R1 and R2 can generate current signals at the same time during the subsequent testing, and the intensity of the testing current signals and the correcting current signals generated is well matched so as to provide testing results of very high accuracy, the electrode R1 can be controlled as the background electrode, and R2 can be controlled as the reference electrode and kept grounded.

On the contrary, if the electrode R2 is detected to generate current first, then this can demonstrate that the user introduces the sample into the test strip from the right. The blood sample can reach R2 first and then R1, so R2 is better covered. Therefore, in this case, R2 can be controlled as the background electrode and R1 can be controlled as the reference electrode (R1 is grounded for protection) to ensure that the electrodes R1 and R2 can generate current signals at the same time during subsequent testing and that the intensity of the current signals generated is well matched. This can ensure accurate testing results of the blood-glucose content.

Control chips can be used to control the voltage of the electrode R1 and the electrode R2 (i.e. the electrodes are made to have the desired electrode function by applying different voltages to the electrode R1 and the electrode R2). If the test determines that the electrode R1 generates current first, then the electrode R1 is applied with a high voltage and the electrode R2 is applied with a low voltage (0 volts) under the control of the chips so that the electrode R1 serves as a background electrode and the electrode R2 serves as a reference electrode. If the test determines that the electrode R2 generates current first, then R2 is controlled as the background electrode by applying a high voltage to R2 and R1 is controlled as the reference electrode applying a low voltage (0 volts) to R1.

Subsequent tests of glucose levels can be performed after reasonable control of the electrodes of the test strip, as based on the direction of sampling.

The real-time information about current generation at the electrodes R1 and R2 of the test strip can be acquired after inserting a test strip, applying a predetermined voltage to the working electrode W of the test strip and applying a sample to the test strip, and determining which electrode generates current first. If the electrode R1 generates current first, then R1 is controlled as the background electrode and R2 is controlled as the reference electrode. Otherwise, R1 is controlled as the reference electrode, and R2 is controlled as the background electrode.

In some embodiments, reasonable control of the electrodes of a test stripe, based on the direction of sampling so as to control the electrode close to the direction of sampling (background electrode or reference electrode) as the background electrode, can avoid the problems where detection signals and correcting signals are not generated at the same time. As well, this can result in mismatching of intensity between detection signals and correcting signals and ensuring accurate detection of current. Therefore, when samples are introduced into a test strip from various directions, the test result of the blood-glucose content can have high accuracy and can reduce waste of test strips due to sample filling.

Embodiment II

Figure 5:
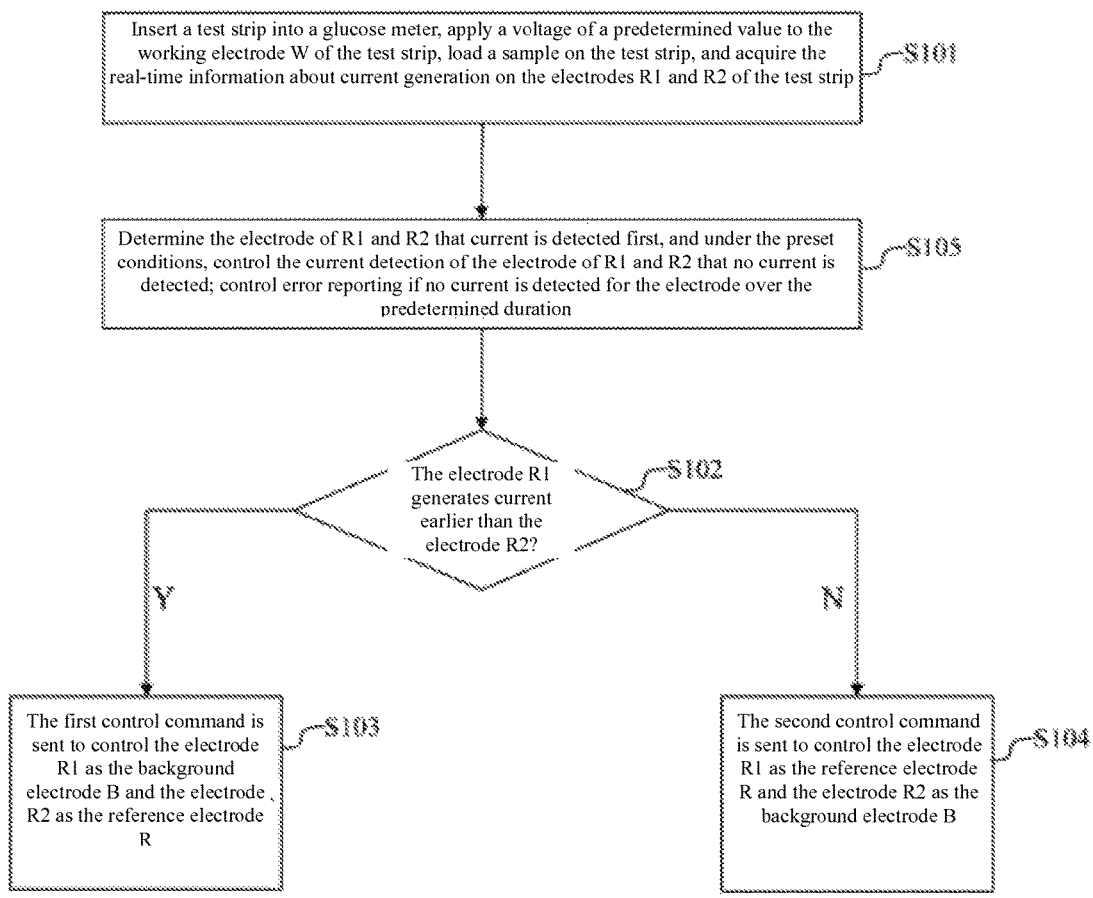
FIG. 5 is another flow diagram of a control method of test strip electrodes disclosed in Embodiment II of the present invention.

Now referring to FIG. 5, the method can also include the following steps: S105: determining which of the electrodes of R1 and R2 generates current first, under the preset conditions, conducting current detection control for the electrode of R1 or R2 which did not generate current, conducting error message reporting if no current is detected for the electrode over the predetermined duration.

Once current is detected at any one of R1 or R2, methods can include terminating application of the voltage to the working voltage W (i.e. the working electrode W outputs a voltage of 0 mv). As well, methods can include keeping R1 and R2 grounded and waiting for 80 ms until sample suction is completed or the sample is fully filled At the end of 80 ms, methods can include controlling the working electrode W to output a pulse in the form of 300 mv(10 ms)–0 mv(30 ms), as well as keeping the electrode that fills the sample first (i.e. the electrode that generates current first) suspended and the other electrode grounded.

When the working electrode W outputs 300 mv, methods can include detecting whether the electrode that absorbs the sample later generates current or not. After current is detected at the electrode that absorbs the sample later, methods can include carrying out current detection at the electrode every 10 ms to perform confirmation twice (a duration of 20 ms) so as to make sure that the current signals are not interfering signals (i.e. the blood sample covers the electrode that absorbs the sample later). If no current is detected at the electrode over 1.5 s, then an error message can be reported (i.e. the blood sample covers the electrode that absorbs the sample later).

In this embodiment, after determining that the electrode which fills the sample first and the electrode which fills the sample later, methods can include leaving the electrode that absorbs the sample later to fill the sample so as to allow the electrode which fills the sample later to be covered by the blood sample. If the electrode is still not covered by the blood sample over the preset duration, an error message can be reported. As a result, the accuracy of the blood-glucose content test can be further improved.

Embodiment III

Figure 6:
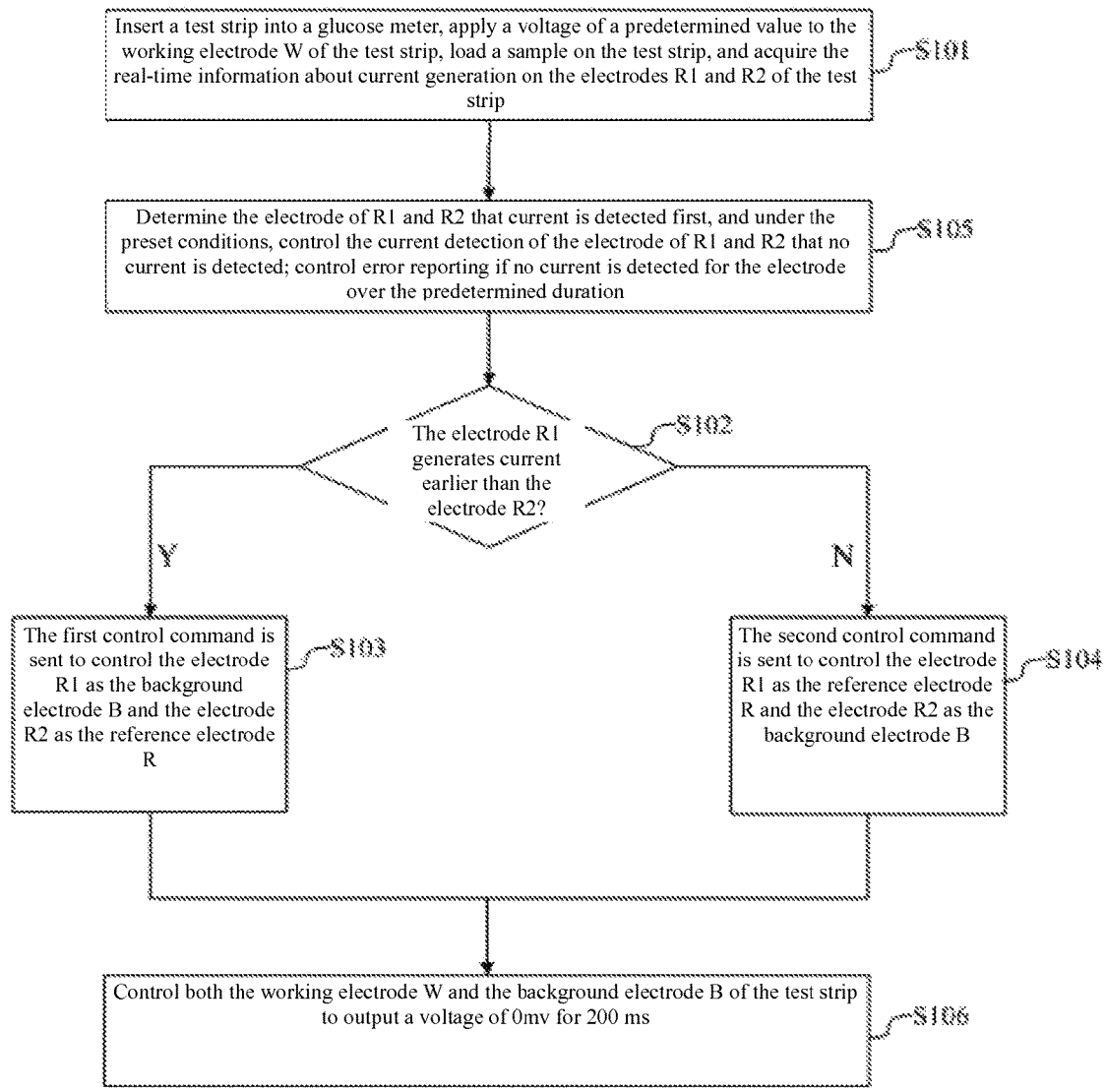
FIG. 6 is another flow diagram of a control method of test strip electrodes disclosed in Embodiment III of the present invention.

Now referring to FIG. 6, methods can also include controlling both the working electrode W and the background electrode B of the test strip to output a voltage of 0 mv for 200 ms (at Step S106).

After a 200 ms-wait, the sample suction stage can be completed. Then the subsequent test of the glucose level can be performed.

After reasonable control of the electrodes of the test strip (i.e. the electrode close to the side of sampling is switched as a background electrode and the electrode away from the side of sampling is switched as a reference electrode) the step can be extended to wait for sample suction so as to ensure that the electrodes of the test strip are completely filled by the blood sample. This can further improve the test result accuracy of the blood-glucose concentration.

Embodiment IV

Embodiment IV discloses a control system for test strip electrodes, which corresponds to the control method for test strip electrodes as disclosed in Embodiments I and III.

Figure 7:
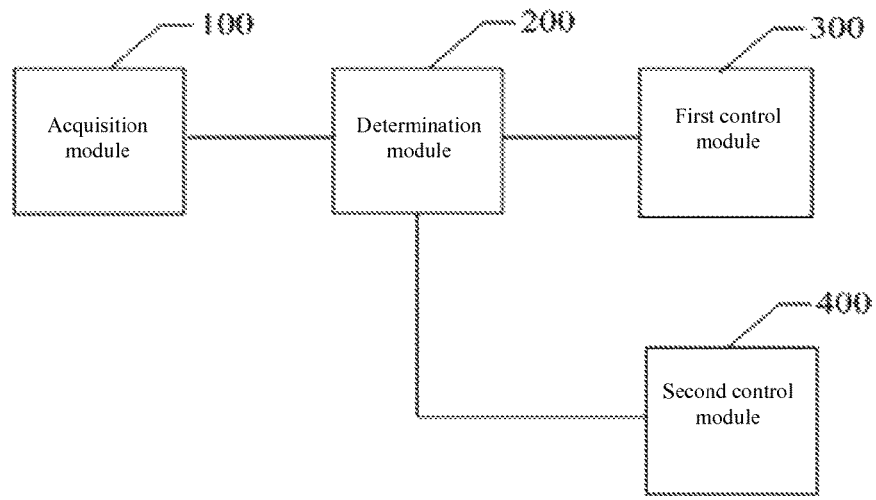
FIG. 7 is a structural diagram of a control system of test strip electrodes disclosed in Embodiment IV of the present invention.

Referring to FIG. 7, the system can comprise an acquisition module 100, a determination module 200, a first control module 300, and the second control module 400.

The acquisition module 100, intended for acquiring the real-time information about current generation at the electrodes R1 and R2 of the test strip after inserting a test strip into a glucose meter, can apply a voltage of a predetermined value to the working electrode W of the test strip, and can apply a sample to the test strip. The acquisition module 100 can comprise the first control module and an acquisition unit.

The first control unit can be intended for controlling the working electrode W to output a voltage of 300 mv continuously. As well, the first control unit can control the electrode R1 and the electrode R2 to be alternately grounded every 10 ms. The electrode that is not grounded of R1 and R2 can be thereby suspended.

An acquisition unit can be intended for controlling the current detection of the grounded electrodes of R1 and R2 in a real-time manner to acquire the real-time information about current generation at the electrode R1 or R2 while the electrode R1 or electrode R2 is grounded. The determination module 200 can be intended for determining whether the electrode R1 generates current earlier than the electrode R2 or not.

The first control module 300 can be intended for sending the first control command to control the electrode R1 as a background electrode B and the electrode R2 as a reference electrode R if electrode R1 generates current earlier than electrode R2.

The second control module 400 can be intended for sending the second control command to control the electrode R1 as a reference electrode R and the electrode R2 as a background electrode B if electrode R1 does not generate current earlier than the electrode R2.

Figure 8:
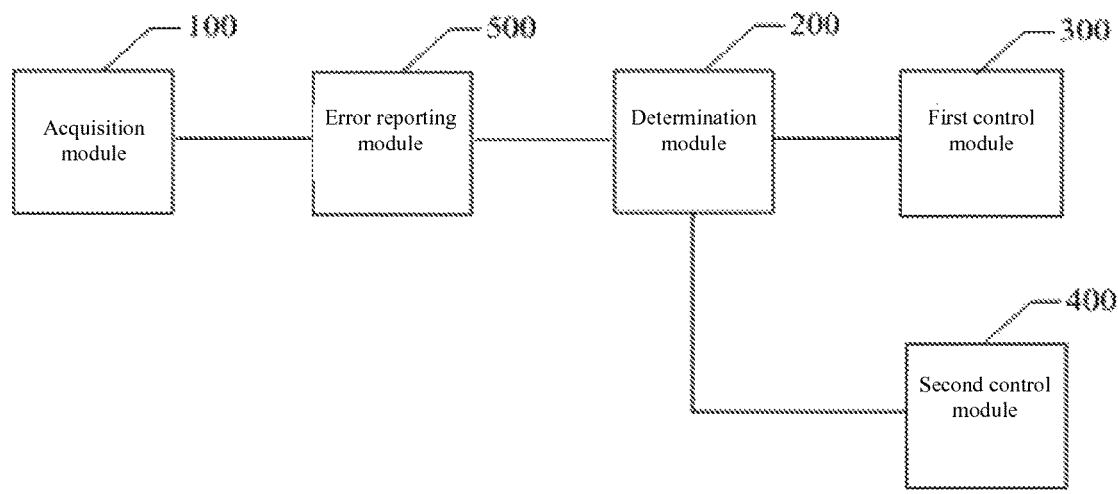
FIG. 8 is another structural diagram of a control system of test strip electrodes disclosed in Embodiment IV of the present invention.

Referring to FIG. 8, the system can also comprise an error message reporting module 500, which can be intended for determining the electrode of R1 and R2 so that current is detected first. Under the preset conditions, the error message-reporting module 500 can control the current detection of the electrode of R1 and R2 so that no current is detected. As well, the error message-reporting module 500 can control error message reporting if no current is detected for the electrode over the predetermined duration. The error message-reporting module 500 can comprise a delay-wait unit, the second control unit, and an error message-reporting unit.

The delay-wait unit can be intended for stopping applying the voltage to the working voltage W, keeping R1 and R2 grounded, and waiting for a 80 ms delay once current is detected at R1 or R2. The second control unit can be intended for controlling the working electrode W to output a pulse in the form of 300 mv-0 mv, as well as controlling the electrodes of R1 and R2 so that current is detected and suspended and the other electrode is grounded after the delay. The error message reporting unit can be intended for acquiring the information about current generation at the grounded electrode. If no current is generated at the grounded electrode over 1.5 s, then the method can include controlling error message reporting.

Figure 9:
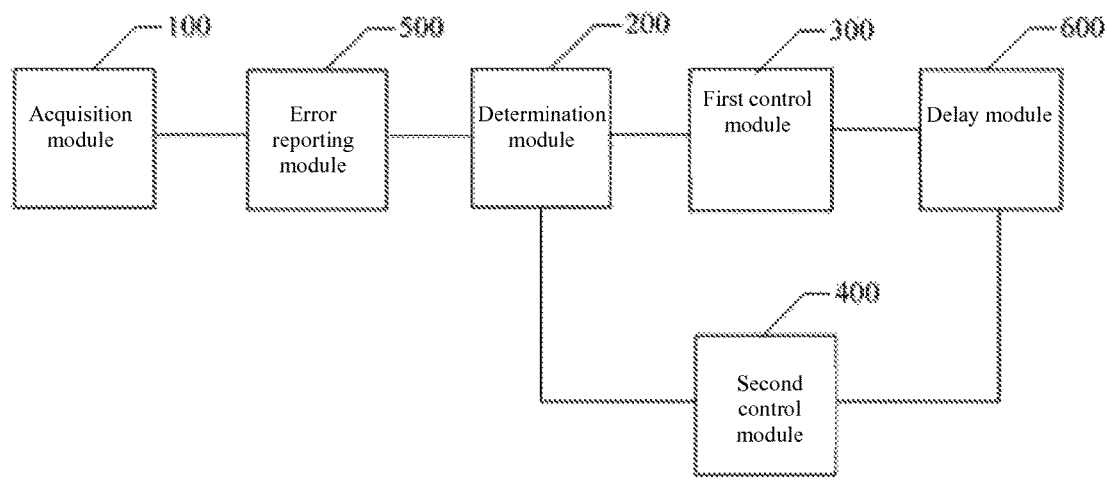
FIG. 9 is a further structural diagram of a control system of test strip electrodes disclosed in Embodiment IV of the present invention.

Referring to FIG. 9, the system can also comprise a delay module 600, which can be intended for controlling both the working electrode W and the background electrode B of the test strip to output a voltage of 0 mv for 200 ms.

Since the control system for test strip electrodes disclosed in Embodiment IV corresponds to the control methods for test strip electrodes disclosed in Embodiment I to Embodiment III, the disclosure only includes a brief description. It should be noted that relevant similarities can be found in the description of the control methods for test strip electrodes disclosed in Embodiment I to Embodiment III, so no further detailed description will be made herein.

In summary, testing, determining, and switching of test strip electrodes can be incorporated into the present invention so that waste of test strips due to sample filling can be reduced when samples are introduced into a test strip from the left, the right, the middle and other directions. This can ensure high accuracy in the final test result of the blood-glucose concentration Differences between each embodiment and the other embodiments are specially described, while mutual reference can be made for the same or similar parts among the embodiments.

The device can be described by treating the functions as various modules or units. As well, the functions of the various modules or units can be implemented in one or multiple software and/hardware in the present invention.

As can be seen from the description of the embodiments, those skilled in the field can clearly understand that the application can be realized by means of software and necessary general-purpose hardware platforms. The technical solution of the application in essence, or the part making contribution to the prior art can be embodied in the form of a software product. The software can be stored in a storage medium, such as ROM/RAM, magnetic disc and/or optical disc. The software can contain a number of instructions to allow a computer device (personal computer, server, network devices, etc.) to execute the method described in the embodiments of or some parts of the embodiments of the application.

The relation terms such as the first, the second, the third, and the fourth are used to distinguish one physical object or operation from another physical object or operation, and are not necessarily intended for requiring or implying any such relation or order among these physical objects or operations. Furthermore, the terms "comprise", "include" or their variants are intended to be non-exclusive so that the process, method, object or equipment comprising a series of elements not only comprises those elements listed, but also can comprise other elements not expressly listed, or also comprises the elements inherent to the process, method, object or equipment. Where there are no more limitations, the element determined by the statement of "comprises a . . . " does not mean that the process, method, object, or equipment comprising the said element also has other same elements.

It should be noted that those skilled in the technical field would understand that some changes or modifications can be made without departure from the principle of the present invention and these changes and modifications shall be considered to fall in the protection scope of the present invention.

What is claimed is:

1. A control method for test strip electrodes, the method comprising:
   inserting a test strip into a glucose meter;
   applying a predetermined voltage to the working electrode W of the test strip;
   applying a sample to the test strip;

acquiring real-time data of current generation at the electrodes R1 and R2 of the test strip; and determining whether the electrode R1 generates current earlier than the electrode R2 or not;

wherein if electrode R1 generates current earlier than electrode R2, a first control command is sent to set the electrode R1 as the background electrode B and the electrode R2 as the reference electrode R;

wherein if electrode R1 does not generates current earlier than electrode R2, a second control command is sent to set the electrode R1 as the reference electrode R and the electrode R2 as the background electrode B;

wherein acquiring the real-time data of current generation on the electrodes R1 and R2 further comprising: setting the working electrode W to output a voltage of 300 mv continuously, and setting the electrode R1 and the electrode R2 to be alternately grounded every 10 ms, wherein the ungrounded electrode of R1 and R2 is suspended; and setting the current detection of the grounded electrode of R1 and R2 in a real-time manner to acquire the real-time data of current generation of electrode R1 or R2 while the electrode R1 or electrode R2 is grounded;

prior to determining whether the electrode R1 generates current earlier than the electrode R2, determining the R1 and R2 electrode, which generated current first; monitoring the R1 and R2 electrode to determine if one of the electrodes did not generate current; and conducting error message reporting if no current is detected for the electrode over a predetermined duration;

once current is detected at R1 or R2, terminating applying the predetermined voltage to a working voltage W, keeping R1 and R2 grounded, and waiting for an 80 ms delay;-after the delay, setting the working electrode W to output a pulse in the form of 300 mv-0 mv, setting R1 and R2 electrode, which generated current first as suspended and the other electrode as grounded; and- acquiring the data on the current generation of the grounded electrode, and if no current is generated at the ground electrode over 1.5s, conducting error message reporting;

setting both the working electrode W and the background electrode B of the test strip to output a voltage of 0 mv for 200 ms.

* * * * *